United States Patent
Boger et al.

(10) Patent No.: US 10,617,433 B2
(45) Date of Patent: Apr. 14, 2020

(54) OSCILLATING DECORTICATION BURR ASSEMBLY

(71) Applicants: David K. Boger, Sonoma, CA (US); William Krauss, Birmingham, AL (US)

(72) Inventors: David K. Boger, Sonoma, CA (US); William Krauss, Birmingham, AL (US)

(*) Notice: Subject to any disclaimer, the term of this patent is extended or adjusted under 35 U.S.C. 154(b) by 405 days.

(21) Appl. No.: 15/499,267

(22) Filed: Apr. 27, 2017

(65) Prior Publication Data

US 2017/0311957 A1    Nov. 2, 2017

Related U.S. Application Data

(60) Provisional application No. 62/328,945, filed on Apr. 28, 2016.

(51) Int. Cl.
*A61B 17/32* (2006.01)
*A61B 17/16* (2006.01)

(52) U.S. Cl.
CPC ...... *A61B 17/1659* (2013.01); *A61B 17/1682* (2013.01); *A61B 17/1686* (2013.01)

(58) Field of Classification Search
CPC .. A61B 17/1664–1693; A61B 17/1659; A61B 17/1662; A61B 2017/564
USPC .......... 606/79–85, 53; 433/119, 51, 86, 114, 433/141–164
See application file for complete search history.

(56) References Cited

U.S. PATENT DOCUMENTS

| | | | | |
|---|---|---|---|---|
| 6,179,839 B1* | 1/2001 | Weiss | ................ | A61B 17/1659 606/280 |
| 6,691,798 B1* | 2/2004 | Lindsay | ................... | B25D 9/04 137/505.12 |
| 2002/0193797 A1* | 12/2002 | Johnson | ............. | A61B 17/1628 606/79 |
| 2005/0075642 A1* | 4/2005 | Felt | .................... | A61B 17/1659 606/89 |
| 2006/0100632 A1* | 5/2006 | Fell | ..................... | A61B 17/1659 606/81 |
| 2006/0111726 A1* | 5/2006 | Felt | .................... | A61B 17/1659 606/86 R |
| 2007/0260253 A1* | 11/2007 | Johnson | ............. | A61B 17/1624 606/79 |
| 2012/0004691 A1* | 1/2012 | Torrie | ................. | A61B 17/1604 606/86 R |
| 2013/0181414 A1* | 7/2013 | Haman | ................. | B27B 19/006 279/144 |

* cited by examiner

*Primary Examiner* — Jessica Weiss
(74) *Attorney, Agent, or Firm* — Erise IP, P.A.

(57) ABSTRACT

An oscillating decorticating burr assembly for decortication of the articular surfaces of joints of the human body is disclosed. The oscillating decorticating burr assembly comprises a burr, a burr-support post, and a handle. Power is imparted to the assembly by way of a user input on the handle causing oscillation of the burr.

16 Claims, 4 Drawing Sheets

OSCILLATING DECORTICATION BURR ASSEMBLY

RELATED APPLICATIONS

This non-provisional patent application claims priority benefit, with regard to all common subject matter, of earlier-filed U.S. Provisional Patent Application No. 62/328,945, filed Apr. 28, 2016, and entitled "OSCILLATING DECORTICATION BURR ASSEMBLY." The identified earlier-filed provisional patent application is hereby incorporated by reference in its entirety into the present application.

BACKGROUND

1. Field

Embodiments of the invention relate to the decortication of the articular surfaces of joints in the human body.

2. Related Art

Various joints within the human body, especially smaller joints such as within the hand and foot, can become arthritic secondary to multiple causes. The arthritis of these joints can cause significant pain and disability. The pain can restrict the ability to perform daily functions such as walking or grasping objects. One of the primary treatments for small joint arthritis is arthrodesis (fusion) of the arthritic joint. In an arthrodesis of a joint, the goal of the surgery is to remove the arthritic joint and allow the two adjacent bones to grow into one continuous bone. Before an arthrodesis can occur, the articular cartilage on the ends of the two adjacent joints must be removed. By removing the articular cartilage and a small amount of subchondral bone directly beneath the cartilage, a high rate of fusion can be achieved.

Traditionally, medical practitioners have removed the articular cartilage and subchondral bone by using a rotary cutting technique. In the traditional technique, the medical practitioner removes the articular cartilage and subchondral bone by applying a rotary cutting tool directly to the articular surfaces of each bone. The traditional technique is disadvantageous for several reasons. First, the traditional technique has a very fast removal rate, which can easily lead to excess material removal of subchondral bone. If excess bone is removed, it can upset the surrounding joint dynamics. Second, the traditional technique can be technically difficult and often requires substantial manipulation and distraction of the joint to expose the articular surface for removal. This can cause trauma to the patient's tissue. Third, the rotatory cutting surfaces are very sharp, and it is not uncommon to have incidental damage to the surrounding soft tissues (skin, tendons, muscle) or to the practitioner's own digits. This can lead a medical practitioner to avoid the procedure, even when it would help the patient.

SUMMARY

Embodiments of the invention solve the above-mentioned problems of the prior art by providing an oscillating decorticating burr for removing the articular cartilage and subchondral bone. The oscillating decorticating burr uses oscillation in lieu of cutting to remove the material. This provides the removal of articular cartilage and subchondral bone at a more controlled pace. This makes the removal of excess material or inadvertent soft tissue damage much less likely. The oscillating decorticating burr also requires less manipulation of the joint, because the oscillating decorticating burr can be fit substantially within the joint space with minimal distraction or manipulation. The oscillating burr can remove the articular cartilage and subchondral bone from both sides of the joint simultaneously thus saving time and improving the fit of the prepared surfaces.

Finally, the oscillating decorticating burr is relatively easy to operate in comparison with the rotary cutting tool, due in part to the more controlled removal and less manipulation required.

A first embodiment of the invention addresses the above-described needs by providing for an oscillating decorticating burr assembly for removing the articular cartilage and subchondral bone comprising a burr for removing the cortical material from the bone at a joint, a burr-support post fixed to the burr and a handle fixed to the burr-support post that a practitioner may grip that imparts an oscillating motion to the burr.

A second embodiment of the invention provides for an oscillating decorticating burr assembly for removing the articular cartilage and subchondral bone comprising a burr permanently attached to a burr-support post for removing cortical material from the bone at a joint, a handle, attached to the burr-support assembly, for imparting an oscillating motion on the burr, wherein the handle comprises a user input for powering the assembly and for adjusting an oscillation speed imparted on the burr.

A third embodiment is disclosed providing a method for removing the articular cartilage and subchondral bone by decortication comprising securing a burr and burr-support post to a handle, wherein the burr is based on a size and a shape of the joint to be decorticated and the burr-support post is attached to a handle, powering the burr to oscillate by manipulating a user input on the handle and placing the oscillating burr against a joint surface for removing a material from the joint.

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the invention will be apparent from the following detailed description of the embodiments and the accompanying drawing figures.

BRIEF DESCRIPTION OF THE DRAWING FIGURES

Embodiments of the invention are described in detail below with reference to the attached drawing figures, wherein.

Figure 1:
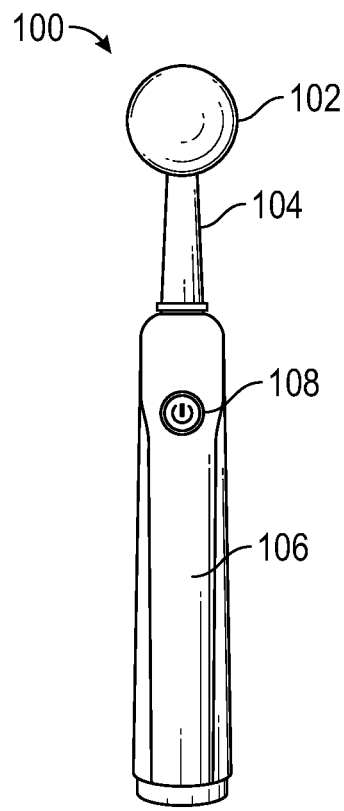
FIG. 1 depicts an exemplary embodiment of the oscillating decorticating burr.

The drawing figures do not limit embodiments the invention to the specific embodiments disclosed and described herein. The drawings are not necessarily to scale, emphasis instead being placed upon clearly illustrating the principles of the invention.

DETAILED DESCRIPTION

The following detailed description of embodiments of the invention references the accompanying illustrations that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the invention. The following detailed description is, therefore, not to be taken in a limiting sense.

In this description, references to "one embodiment", "an embodiment", "embodiments", "various embodiments", "certain embodiments", "some embodiments", or "other embodiments" mean that the feature or features being referred to are included in at least one embodiment of the technology. Separate references to "one embodiment", "an embodiment", "embodiments", "various embodiments", "certain embodiments", "some embodiments", or "other embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the current technology can include a variety of combinations and/or integrations of the embodiments described herein.

As shown in FIG. 1, the oscillating decorticating burr 100 generally includes a burr 102, a burr-support post 104, and a handle 106. The burr 102 is configured to remove the cortical material from the bone at the joint. The burr 102 is configured to oscillate. The burr may be placed on the cortical material while oscillating so as to remove a portion of the material. The burr is secured to a burr-support post 104. The burr-support post 104 attaches the burr 102 to the handle 106. The handle 106 provides the oscillating motion to the burr 102 (by any of the various power methods discussed below). The handle 106 is gripped by the medical practitioner to perform the procedure.

As can be seen in FIG. 1, the burr 102 is secured on the burr-support post 104 to allow the burr 102 to be manipulated into the desired location and orientation. The burr 102 is a partially spherical, hemi-spherical, or other arcuate shape. As shown in FIG. 1, the burr 102 may be a generally flattened hemi-spherical shape. In some embodiments, the burr 102 may present a convex side (as visible in FIG. 1) and a concave side (from a view opposite of FIG. 1, not shown). This may allow the burr 102 to fit within the joint. Depending on the joint or joints, different sizes and shapes of burr 102 may be used. The radii of the burr may closely match the dimensions of the joint to be fused.

The burr 102 presents a roughened surface on both faces. The roughened surface removes the cortical material by oscillating against the surface. The roughened surface is sufficiently durable to remove the cortical material without disintegrating. The burr 102 may also present a notch, a recess, or another structure for receiving and being secured to the burr-support post 104, such as shown in FIG. 1 and described below.

The roughened surface of burr 102 may be formed of various hardened materials. The material used may be durable enough to be used in multiple operations without significant deterioration. The material in this scenario may be thoroughly cleaned and sanitized between operations as to avoid contamination. In embodiments, the material may be a low-cost material that may only last for the duration of one operation. This procedure allows for a disposable burr that does not significantly increase the cost. In this scenario, a new burr per procedure is used which ensures that there is no contamination from previous operations.

In embodiments of the invention, the burr 102 will come in many different sizes and shapes that may be based upon the size and shape or other characteristics of the joint to be fused. For example, the burr 102 may substantially match the size of the joint. This allows the medical practitioner to apply the burr 102 within the joint easily. The medical practitioner may select a burr 102 of a certain outer diameter, thickness and spherical radius. For example, a burr 102 may be 15 mm in diameter and 2 mm thick, such as shown in FIG. 2. Based upon the joint designed to be used with, the burr 102 may be 5-100 mm in diameter and 1-10 mm in thickness.

The shape of burr 102 may be round, square, triangular, or any shape that may be beneficial to the efficiency of the procedure. In embodiments, the burr 102 may be pointed in the same manner as a dental scraper for better accuracy, or a brush for cleaning. It should therefore be appreciated that various embodiments of the invention may utilize burrs of various sizes, shapes, materials, and configurations to perform various functions.

The burr-support post 104 secures the burr 102 to the handle 106. In embodiments of the invention, the burr 102 is permanently secured to the burr-support post 104. The medical practitioner therefore changes the burr 102 by removing the burr-support post 104 from the oscillating handle 106. In other embodiments, the burr 102 is selectively secured to the burr-support post 104. In these embodiments, the medical practitioner removes the burr 102 from the burr-support post 104 in order to use the correctly-sized burr. The burr 102 may be detachable from the burr-support post 104 and the burr-support post 104 may be detachable from the handle 106 in the same embodiment. In still other embodiments, the burr 102 is a cover configured to be emplaced over a portion of the burr-support post 104. In these embodiments, the burr is slipped onto and off of the burr-support post by the medical practitioner.

Figure 2A:
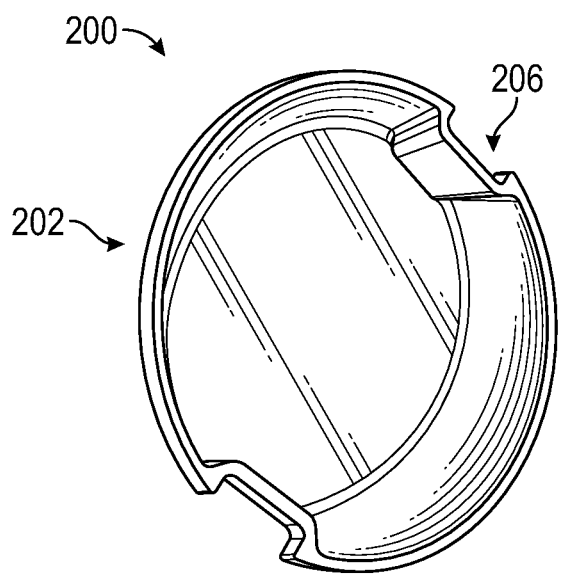
FIG. 2A depicts an exemplary embodiment of the decorticating burr.
Figure 2B:
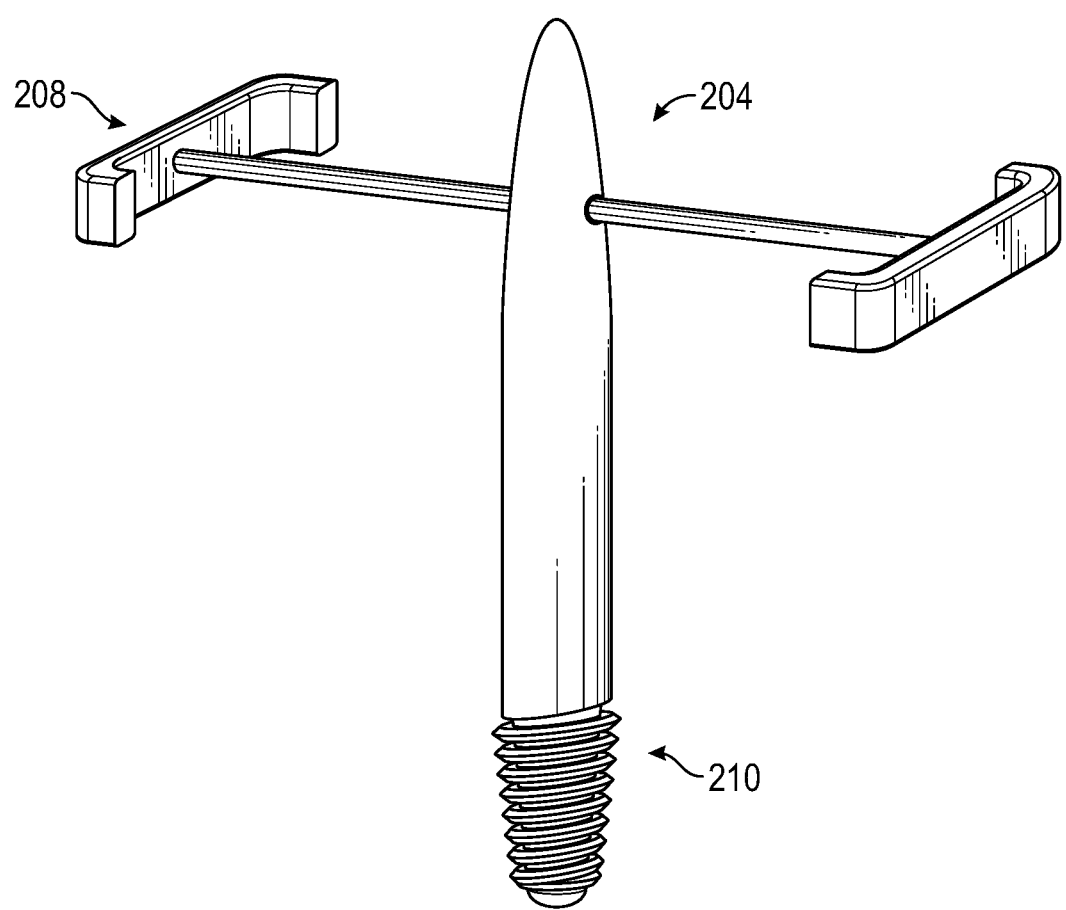
FIG. 2B depicts an exemplary embodiment of the decortication burr assembly.

Referring now to an exemplary embodiment depicted in FIGS. 2A and 2B, the interface between the burr 202 and the bur-support post 210 is represented on the burr 202 in FIG. 2A and the burr-support post 204 in FIG. 2b. In this embodiment, the burr 202 has two indentions 206. These indentions 206 correspond to hooks 208 on the burr-support post 204. The burr 202 is snapped into the hooks 208 on the burr-support post 204. As such, the burr 202 is retained within the burr-support post 204 and may be selectively removed such that another burr (such as of a different size or shape) may be added.

In embodiments of the invention, various configurations of the burr-support post 204 may be used. As depicted in FIG. 2B a hook 208 may be utilized to grasp the burr. In some embodiments, as depicted, there are two hooks 208 that are each are two sided and configured horizontally, or perpendicular to the burr-support post. In other embodiments of the invention, the hooks 208 are be configured to attach the burr 102 to one side of the burr-support post and the attachments may be configured vertically, or parallel to the burr-support post, not illustrated. The attachment between the burr 202 and the burr-support post 204 may be, but is not limited to, fasteners, clamps, screws, and adhesive. The burr 202 may also be permanently attached to the burr-support post, or molded, or cast as one.

The burr-support post 204 is generally elongated so as to present a distal end and a proximal end. The distal end has attachments for the burr 202 to be disposed thereon. The proximal end includes a handle interface for selectively securing to the oscillating handle 106. In embodiments of the invention, the burr-support post 104 is generally tapered from the proximal end to the distal end. The proximal end (as well as the handle 106) is relatively thick and wide so as to be easily grasped and manipulated by the medical practitioner. The distal end is relatively thin so as to not interfere with the application of the burr to the joint, while providing the structural support necessary to withstand the oscillations and allow for the medical practitioner to exert force again the joint. The distal end may also be telescoping. This may aid the practitioner in reaching the joints and allow the distal end of the burr support post to be slightly narrower.

The burr-support post 204 can be attached to the handle 106 in different ways. In the exemplary embodiment depicted in FIG. 2B, the burr-support post has a screw type attachment 210 for screwing into the handle 106 which has a corresponding attachment. The burr-support post 204 may also be attached to the handle 106 by a snapping mechanism, adhesive, or any other method that may be beneficial. The attaching mechanism may be adjustable within the handle 106 housing allowing the burr-support post 204 to be placed at different angles. This may help the practitioner to get the burr 202 into the correct orientation for the procedure. The burr-support post 204 and handle 106 may also be molded or cast as one unitary structure or permanently attached to one another such as via a chemical adhesive, a mechanical clip, or a mechanical fastener.

Referring again to FIG. 1, the handle 106 is configured to be gripped by the medical practitioner and to provide the oscillations to the burr 102. The handle 106 provides a relatively large and stable structure to be gripped. In some embodiments, the handle 106 is generally cylindrical. The handle 106 may be tapered from a proximal end to a distal end, as discussed above, or the handle 106 may be linear (as shown in FIG. 1). The handle 106 may also integrate with a stand, a charger, or another support mechanism. This keeps the burr 102 from touching anything, so as to prevent contamination and foreign materials from being transferred to the joint from the burr 102. The handle may have a cord for connecting to a power supply or wall outlet. The battery may also be charged from the power supply or wall outlet.

Referring again to the exemplary embodiment in FIG. 1, the handle 106 is configured to receive the burr-support post 104 (and by extension, the burr 102) at a post interface. The post interface secures, captures, adheres, or otherwise attaches to the burr-support post. The post interface keeps the burr-support post 104 secured and aligned, so as to allow the medical practitioner to perform precise movements with the oscillating decortication burr assembly.

The handle 106 is configured to be gripped by the user. In embodiments, the handle may be covered with a soft gripping material such as, foam, rubber, latex, or gel. This type of material may aid in gripping the handle without slipping. The handle may be shaped to fit a human hand with ridges where fingers can comfortably grip. These ridges and the size of the handle may be different for different sized hands or as preferred by the practitioner.

The handle 106 may present a power button 108 or another input to begin operations. In some embodiments, the handle 106 is powered by a battery and a piezoelectric transducer. The battery and the transducer impart the oscillating motion on the burr 102 based upon the actuation of the power button 108 or other input. For example, the battery and transducer may create an oscillation of approximately 240 Hz. In other embodiments, the battery and transducer may create oscillations in the range of 100-10,000 Hz, depending on the consistency of the material to be removed, the strength of the underlying bone, the capabilities of the handle 106, and other factors. In other embodiments, the handle may be powered by alternating current electrical power, hydraulic power, pneumatic power, mechanical power, or other power source. The handle may therefore interface with a cable, line, or cord for supplying this power.

In the exemplary embodiment depicted in FIG. 1, the user input is a button 108. This button provides power to the burr assembly 100 and begins the burr 102 oscillation. The oscillation may be a setting chosen prior to powering the assembly or it may be a one setting device. In other embodiments, the user input may be a knob, switch, or roller switch with multiple settings. The user input may be used to provide different levels of oscillation from fast to slow depending on the desired speed for the particular operation. This speed may be in the range of 100-10,000 Hertz as described above, or in another range based upon the application.

Figure 3:
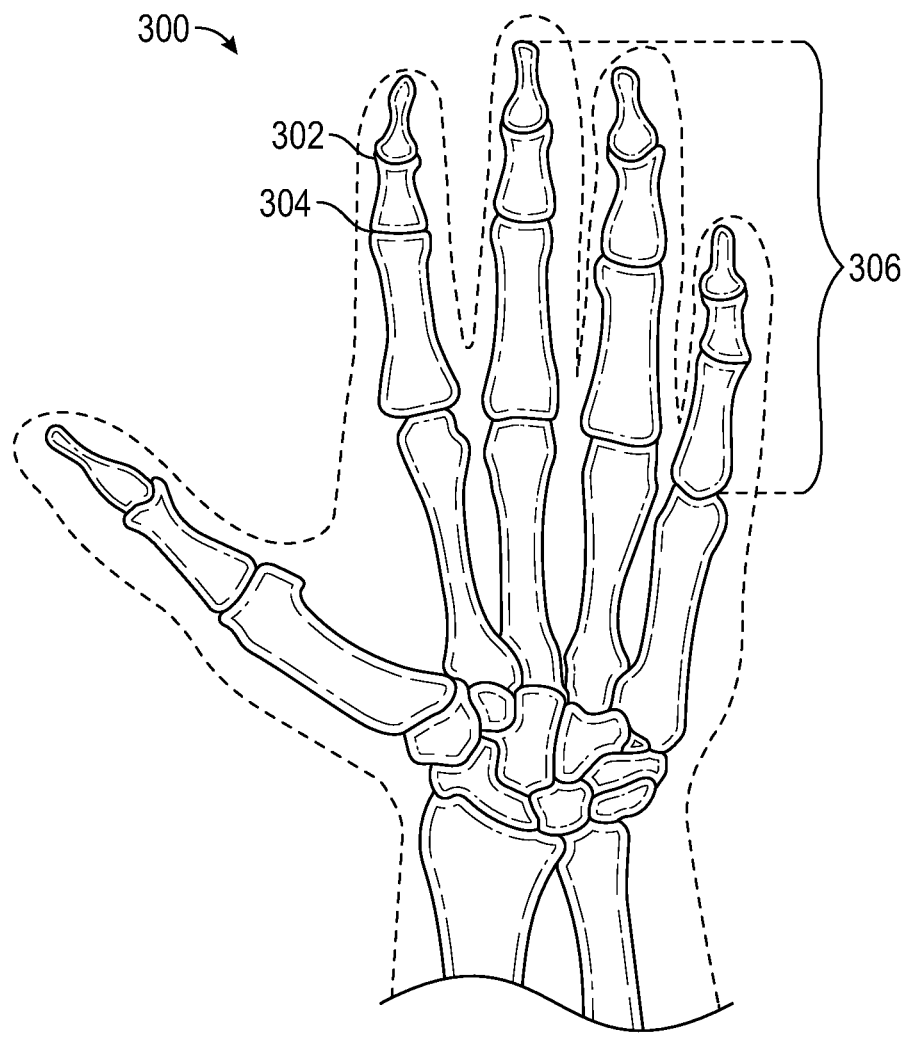
FIG. 3 depicts a skeletal hand displaying the operating joints.

A method of using the oscillating decortication burr assembly will now be discussed. The medical practitioner diagnoses arthritis of a joint. For example, FIG. 3 shows the bones of the hand and fingers. Embodiments of the invention may be used to remove the articular cartilage and subchondral bone from between any of these bones. The joints of the finger (commonly known as a distal interphalangeal joint 302 and a proximal interphalangeal joint 304, located between the respective phalanges 306) may require the discussed procedure, for example.

The medical practitioner applies an anesthetic. Following the anesthetic, the medical practitioner will incise the skin and expose the joint to allow access to the joint. The medical practitioner will then retract the tissue from around the joint, such as muscles, tendons, fat, and the like. The medical practitioner is ensuring that the joint is fully exposed so as to prevent collateral trauma to the surrounding tissue. The medical practitioner may then manipulate or distract the joint to expose the space between the joint surfaces as much as necessary. While not requiring as much physical manipulation as in the procedures of the prior art, some manipulation and/or compression may be necessary to expose the interior of the joint.

The medical practitioner also selects the burr 102 based upon the size and shape of the joint. In some instances, the medical practitioner may select the burr 102 before beginning the procedure, relying on standard joint sizes, approximations, X-ray scan information, external measurements, or other information. In other instances, the medical practitioner may select the burr 102 after the joint is exposed such that the medical practitioner has a more precise understanding of the size and shape of the joint. Once the burr 102 is selected, the practitioner will secure the burr-support post 104 of the selected burr 102 to the handle 106.

With the joint exposed and the burr 102 installed, the medical practitioner grasps the handle 104 of the oscillating decortication burr assembly and applies power using by manipulating the user input 108. The oscillating decortication burr assembly will then begin oscillating. In some embodiments, the medical practitioner may select the speed of oscillation. This speed may be applied by the user input 108. In other embodiments, the speed of oscillation may be the same for all instances. The medical practitioner then places the oscillating burr 102 against the joint surfaces to begin removing the articular cartilage and subchondral bone therefrom. In some embodiments, the medical practitioner may insert the burr 102 into the joint surface and then apply the power so as to allow the burr 102 to be fully within the joint. The oscillating burr 102 will then remove the articular cartilage and subchondral bone in a slow and controlled manner. The medical practitioner may adjust the angles and compression placed on the burr 102 and the affected digit to remove material and achieve the alignment as desired.

Upon completion, the medical practitioner will remove the burr 102 from the joint, stop the power, irrigate the joint, align the joint, and then fixate the arthrodesis site and suture the wound. When the arthrodesis site has fused successfully, the patient will experience decreased pain and increased functionality in their daily activities.

In an embodiment, a method for removing the articular cartilage and subchondral bone by decortication is disclosed. A practitioner incises the skin to allow for pulling the skin back and exposing a joint to be decorticated. When the skin is pulled back the joint is fully exposed to allow full access and to prevent collateral trauma to the surrounding tissue.

Figure 4:
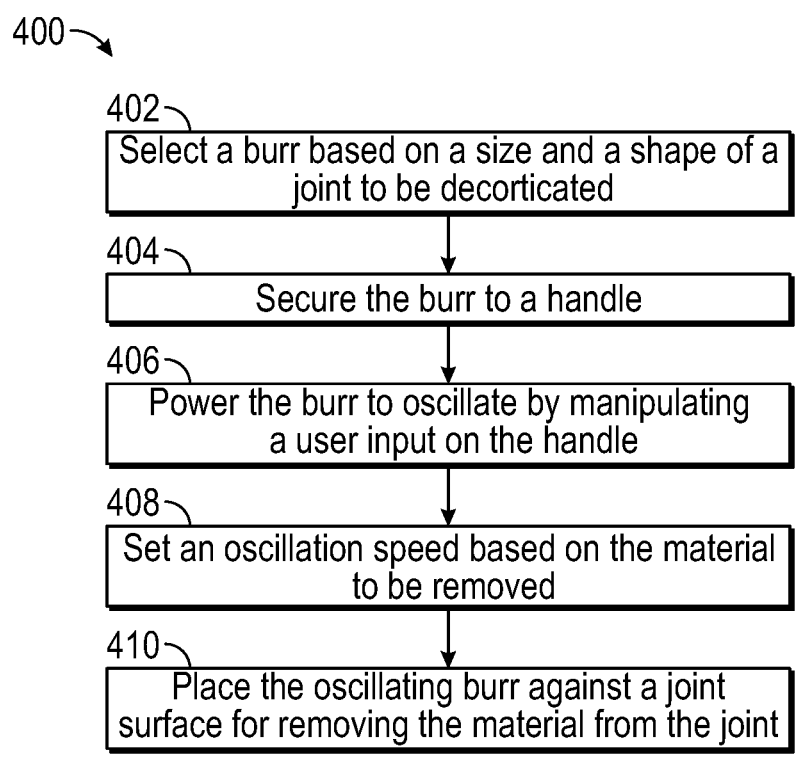
FIG. 4 depicts a method for implementing the decorticating burr assembly.

Referring to FIG. 4, exemplary steps of a method are shown. In Step 402 the practitioner first selects a burr based on a size and a shape of a joint to be decorticated. In this particular embodiment, the burr is secured to a burr-support post however, this is exemplary only and the burr and post may be separate and selectively attachable. Next, in Step 404, the practitioner completes the assembly by securing the burr to the handle. This may be performed using any of the attachments described above.

In Step 406 the practitioner provides power to the assembly by manipulating the user input on the handle. The power starts the burr oscillating. In Step 408, the practitioner sets the speed of the oscillation based on the material to be removed. In Step 410, the practitioner places the oscillating burr against the joint surface. The oscillation of the burr against the material, in this case articular cartilage, causes the material to break apart from the bone. Once the operation is complete the practitioner removes the burr and stops power to the burr. The joint is then irrigated and re-aligned and the wound sutured.

It should be noted that the decortication of joints is used in this application as an exemplary field and that joints other than hand joints may be decorticated. The oscillating decortication burr assembly may be used in other fields, such as for the removal articular cartilage and bone or other materials.

Although the invention has been described with reference to the embodiments illustrated in the attached drawing figures, it is noted that equivalents may be employed and substitutions made herein without departing from the scope of the invention.

The invention claimed is:

1. A method for removing articular cartilage and subchondral bone by decortication comprising:
   selecting a burr based on a size and a shape of a joint to be decorticated,
   wherein the joint to be decorticated is one of a human hand joint or a human foot joint;
   securing the burr to a handle,
   wherein the burr is secured to the handle by attaching a burr support post of the burr to the handle, wherein the burr support post comprises a proximal end and a distal end, and wherein the proximal end includes a handle interface for selectively securing to the handle;
   powering the burr to oscillate by manipulating a user input on the handle;
   setting an oscillation speed based on a material of the joint to be removed;
   inserting the burr into the joint,
   wherein the burr comprises a concave burr wall to fit within the joint; and
   placing the oscillating concave burr wall against a joint surface of the joint and removing the material from the joint.

2. The method of claim 1, further comprising the following steps:
   incising a patient's skin to create an opening;
   pulling the patient's skin back allowing access to the joint and fully exposing the joint to prevent collateral trauma to surrounding tissue;
   removing the burr from the joint and stopping power to the burr;
   irrigating and aligning the joint; and
   suturing the opening.

3. The method of claim 1, wherein the step of selecting the burr is further based upon the material of the joint to be removed.

4. The method of claim 1, wherein the burr is sized to fit substantially within the joint so as to require minimal distraction or manipulation of the joint.

5. The method of claim 1, wherein the oscillation speed is set in a range with a maximum of 10,000 Hertz and a minimum of 100 Hertz.

6. The method of claim 1, wherein the joint is a distal interphalangeal joint.

7. The method of claim 1, wherein the joint is a proximal interphalangeal joint.

8. The method of claim 1, wherein:
   the burr is disposable; and
   the burr is new to ensure no contamination from a previous procedure is transferred to the joint.

9. A method of removing articular cartilage and subchondral bone from a human hand joint by decortication comprising:
   selecting a burr based on a size and a shape of the burr, wherein the size and the shape of the burr are configured to fit within the human hand joint to be decorticated;
   securing the burr to a handle,
   wherein the burr is secured to the handle by attaching a burr support post of the burr to the handle, wherein the burr support post comprises a proximal end and a distal end, and wherein the proximal end includes a handle interface for selectively securing to the handle;
   powering the burr to oscillate by manipulating a user input on the handle;
   setting an oscillation speed based on a material of the human hand joint to be removed;
   inserting the burr into the human hand joint,
   wherein the burr comprises a concave burr wall to fit within the human hand joint; and
   removing the material from the human hand joint by placing the oscillating concave burr wall against a joint surface of the human hand joint.

10. The method of claim 9, wherein the burr is at least partially spherical having at least one radii and the at least one radii of the burr is sized to closely match a dimension of the human hand joint.

11. The method of claim 9, further comprising the following steps:
   incising a patient's skin to create an opening;

pulling the patient's skin back allowing access to the human hand joint and fully exposing the human hand joint to prevent collateral trauma to surrounding tissue;
removing the burr from the human hand joint and stopping power to the burr;
irrigating and aligning the human hand joint; and
suturing the opening.

12. The method of claim 9, wherein the step of selecting the burr is further based upon the material of the human hand joint to be removed.

13. The method of claim 9, wherein the human hand joint is an interphalangeal joint.

14. A method for removing articular cartilage and subchondral bone from a human foot joint by decortication comprising:
selecting a burr based on a size and a shape of the burr, wherein the size and the shape of the burr are configured to fit within the human foot joint to be decorticated;
securing the burr to a handle, wherein the burr is secured to the handle by attaching a burr support post of the burr to the handle, wherein the burr support post comprises a proximal end and a distal end, and wherein the proximal end includes a handle interface for selectively securing to the handle;
powering the burr to oscillate by manipulating a user input on the handle;
setting an oscillation speed based on a material of the human foot joint to be removed;
inserting the burr into the human foot joint, wherein the burr comprises a concave burr wall to fit within the human foot joint; and
removing the material from the human foot joint by placing the oscillating concave burr wall against a joint surface of the human foot joint.

15. The method of claim 14, wherein:
the burr is disposable; and
the burr is new to ensure no contamination from a previous procedure is transferred to the human foot joint.

16. The method of claim 14, further comprising the following steps:
incising a patient's skin to create an opening;
pulling the patient's skin back allowing access to the human foot joint and fully exposing the human foot joint to prevent collateral trauma to surrounding tissue;
removing the burr from the human foot joint and stopping power to the burr;
irrigating and aligning the human foot joint; and
suturing the opening.

* * * * *